United States Patent [19]
Berndt

[11] Patent Number: 6,080,574
[45] Date of Patent: Jun. 27, 2000

[54] COMPOSITE OPTICAL BLOOD CULTURE SENSOR

[75] Inventor: Klaus W. Berndt, Timonium, Md.

[73] Assignee: Becton, Dickinson and Company, Franklin Lakes, N.J.

[21] Appl. No.: 09/262,520

[22] Filed: Mar. 4, 1999

Related U.S. Application Data

[63] Continuation-in-part of application No. 08/617,966, Mar. 11, 1996, abandoned, which is a continuation of application No. 08/244,228, May 10, 1994, abandoned.

[51] Int. Cl.[7] .................................................. C12M 1/34
[52] U.S. Cl. ..................................... 435/288.7; 422/82.08
[58] Field of Search ...................... 435/288.7; 422/82.08, 422/82.09; 436/172

[56] References Cited

U.S. PATENT DOCUMENTS

| | | | |
|---|---|---|---|
| 4,851,195 | 7/1989 | Matthews et al. | 422/68 |
| 4,945,060 | 7/1990 | Turner et al. . | |
| 5,030,420 | 7/1991 | Bacon et al. | 422/82.07 |
| 5,217,876 | 6/1993 | Turner et al. | 435/34 |
| 5,372,784 | 12/1994 | Morris et al. | 422/82.08 |

FOREIGN PATENT DOCUMENTS

| | | |
|---|---|---|
| 0 448 923 A1 | 10/1991 | European Pat. Off. . |
| 0 590 775 A1 | 4/1994 | European Pat. Off. . |
| 2 132 348 | 7/1994 | United Kingdom . |

OTHER PUBLICATIONS

"BacT/Alert: An Automated Colorimetric Microbial Detection System", Thorpe et al,. Journal of Clinical Microbiology, vol. 28, No. 7, Jul. 1990, pp. 1608–1612.

*Primary Examiner*—David A. Redding
*Attorney, Agent, or Firm*—Bruce S. Weintraub, Esq.

[57] ABSTRACT

A culture medium and blood specimen are introduced into a sealable glass vial having a headspace gas mixture such that a change in the gas mixture composition can be monitored by a chemically sensitive material in the vial comprising a mixture of a fluorophore and a chromophore. The fluorophore exhibits a long fluorescence decay time and a fluorescence intensity that depend on a first chemical parameter, such as oxygen concentration. The chromophore exhibits an optical transmission that depends on a second chemical parameter, such as carbon dioxide concentration, the optical transmission of the chromophore changing with the second chemical parameter either within the excitation or within the emission wavelength range of the fluorophore.

12 Claims, 9 Drawing Sheets

FIRST DERIVATIVE OF FLORESCENCE INTENSITY / MODULATION DEGREE

TIME (HOURS)

FIG. 9

FLUORESCENCE INTENSITY

TIME (HOURS)

FIG. 10

FLORESCENCE INTENSITY / MODULATION DEGREE

TIME (HOURS)

FIG. 11

FIRST DERIVATIVE OF FLORESCENCE INTENSITY / MODULATION DEGREE

TIME (HOURS)

COMPOSITE OPTICAL BLOOD CULTURE SENSOR

This is a continuation-in-part application of U.S. patent application Ser. No. 08/617,966 filed on Mar. 11, 1996, now abandoned which is a continuation of U.S. patent application Ser. No. 08/241,228 filed on May 10, 1994, now abandoned.

BACKGROUND OF THE INVENTION

The present invention relates to a non-invasive method and apparatus for detecting biological activities in a fluid specimen, such as blood, urine or sputum, where the specimen and a culture medium are introduced into sealable containers and are exposed to conditions enabling a variety of metabolic, physical, and chemical changes to take place in the presence of microorganisms in the sample. The biological activity being detected by a variety of chemical sensors that are based on changes in fluorescence lifetime and/or intensity.

Usually, the presence of microorganisms such as bacteria in a patient's body fluid, particularly blood, is determined using blood culture vials. A small quantity of blood is injected through a sealing rubber septum into a sterile vial containing a culture medium. The vial is incubated at a temperature conducive to bacterial growth, e.g., 37° C., and monitored for such growth.

Common visual inspection involves monitoring the turbidity of the liquid suspension. Known instrumental methods detect changes in the $CO_2$ content in the headspace of the culture bottles, which is a metabolic by-product of the bacterial growth. Monitoring the $CO_2$ content can be accomplished by conventional methods, including radiochemical, infrared absorption at a $CO_2$ spectral line, or pressure/vacuum measurement. These methods, however, require invasive procedures which can result in cross-contamination between vials.

Recently, novel non-invasive methods have been developed which use chemical sensors inside a vial. Such sensors often respond to changes in the $CO_2$ concentration by changing their color or by changing their fluorescence intensity. The outputs from these sensors are based upon light intensity measurements. This means that errors may occur, particularly if the light sources used to excite the sensors, or the photodetectors used to monitor intensities, exhibit aging effects over time.

In known automated non-invasive blood culture systems, individual light sources, individual spectral excitation and emission filters, and individual photodetectors are arranged adjacent to each vial. Such arrangements result in certain station sensitivity variations from one vial to the next. Due to the fact that most known blood culture sensors generate only a moderate contrast ratio in the measured photocurrent during bacterial growth, extensive and time-consuming calibration procedures and sophisticated detection algorithms are required to operate these systems. Moreover, light sources, spectral filters, and photodetectors with extreme narrow specification tolerances must be utilized.

The disadvantage of such intensity-based sensor arrangements can be overcome by utilizing fluorescent sensors that change their fluorescence lifetime, wherein intensity measurement is replaced with time parameter measurement and intensity changes have no impact on the sensor output signal. Many chemical sensor materials are known that change their fluorescence lifetime with changing oxygen concentration, pH, carbon dioxide concentration, or other chemical parameters (see, e.g., G.B. Patent No. 2,132,348).

A change in sensor fluorescence lifetime is commonly monitored by applying a well-known phase shift method (see, e.g., U.S. Pat. No. 5,030,420), wherein the excitation light is intensity-modulated. That method results in an intensity-modulated fluorescence emission that is phase-shifted relative to the excitation phase. Phase shift angle, $\theta$, being dependent on the fluorescence lifetime, $\tau$, according to the equation:

$$\tan \theta = \omega \tau \qquad (1)$$

where $\omega = 2\pi f$, is the circular light modulation frequency.

An inspection of equation (1) reveals that the phase shift method allows for maximum resolution, $d\theta/d\tau$, under the condition $\omega\tau=1$. Unfortunately, almost all known pH- or carbon dioxide-sensitive fluorophores have decay times in the range 5 ns to 500 ps. In other words, light modulation frequencies, $f=\frac{1}{2}\pi\tau$, in the range 32 MHz to 320 MHz would be required.

It is possible to accomplish light intensity modulation at such high frequencies, however, this would require acousto-optic or electro-optic modulators which are only efficient in combination with lasers. Moreover, detecting the modulated fluorescence light would require highly sensitive high-speed photodetectors, such as microchannel-plate photomultipliers, which are rather expensive. Consequently, all commercial automated blood culture systems are based on intensity monitoring, and none utilize time-resolved fluorescent carbon dioxide sensors.

SUMMARY OF THE INVENTION

The present invention overcomes problems identified in the art by providing a method and apparatus for reliably and non-invasively detecting biological activities in blood culture vials that do not have the fluorescence intensity limitations discussed above.

According to the present invention, a culture medium and blood specimen are introduced into a sealable glass vial having a headspace gas mixture such that a change in the gas mixture composition can be monitored by a chemically sensitive composite material in the vial. The chemically sensitive composite material comprises a mixture of a fluorophore and a chromophore. The fluorophore exhibits a long fluorescence decay time and a fluorescence intensity that depend on a first chemical parameter, such as oxygen concentration. The chromophore exhibits an optical transmission that depends on a second chemical parameter, such as carbon dioxide concentration, the optical transmission of the chromophore changing with the second chemical parameter either within the excitation or within the emission wavelength range of the fluorophore.

By illuminating the composite sensor matrix with intensity-modulated light, measuring the AC component and the DC component of the fluorescence photocurrent separately, and by processing these signals in a computer, a sensor output signal is produced that shows a significantly increased contrast ratio, compared with known optical blood culture sensors. In addition, the composite sensor allows for separation of the oxygen consumption effect and the carbon dioxide production effect, and requires only a relatively low light modulation frequency (150 kHz). Therefore, a low-cost light emitting diode (LED) can be used as the excitation source.

More particularly, the fluorophore and the chromophore are mixed into the same sensor matrix and are illuminated with intensity-modulated excitation light. The modulation frequency is chosen so that the condition $\omega\tau=1$ holds for the fluorophore when the fluorescence lifetime has its minimum value. The fluorescence light emitted by the composite sensor is monitored using only one photodetector. The fluorescence photocurrent from the photodetector is split into its AC and DC components, that are measured separately. A sensor output signal is then generated by dividing the measured DC component by the calculated fluorescence modulation degree, which is equal to the AC/DC ratio of the components.

In an aerobic vial, bacterial growth causes at first a decrease in the oxygen concentration. This, in turn, results in an increase in the fluorescence intensity and in the fluorescence lifetime of the fluorophore. If the light modulation frequency for the excitation source is selected properly, the increase in lifetime causes a decrease in the fluorescence modulation degree. As soon as carbon dioxide is produced by the bacteria, the chromophore's optical transmission increases, which results in a further amplification in the emitted fluorescence intensity. In a sensor arrangement according to the present invention, the combined effects of oxygen consumption and carbon dioxide production generate a significantly higher change in the measured fluorescence photocurrent than in known blood culture sensors.

As mentioned above, the fluorescence modulation degree is also calculated. The modulation degree can be measured at very high precision because all artifacts due to light source aging, optical filter variations, vial displacement, and photodetector sensitivity changes are canceled out. Therefore, it is practical to utilize the modulation degree to calculate a final sensor output signal. This final signal is obtained by dividing the increasing DC component by the decreasing modulation degree. Due to the opposite trends of these two quantities, a further amplification effect results with regard to the final sensor output signal. Consequently, the sensor output signal shows a contrast ratio due to bacterial growth that is larger by almost two orders of magnitude as compared to known blood culture sensors. This allows for better detection, and the requirements with regard to part's tolerances are reduced.

In general, a time delay is observed between oxygen consumption and carbon dioxide production. Therefore, analyzing the final sensor output signal allows for the separation of the two effects. By taking into account the magnitude, speed, time of occurrence and relative time delay between the two mechanisms (oxygen and carbon dioxide), information regarding the microorganism species can be gained. Moreover, even if no time delay should occur, the two mechanisms can be resolved by analyzing the fluorescence modulation degree, as explained below.

These and other features, objects, benefits and advantages of the present invention will become more apparent upon reading the following detailed description of the preferred embodiments, along with the appended claims in conjunction with the drawings, wherein reference numerals identify corresponding components.

DETAILED DESCRIPTION

Figure 1:
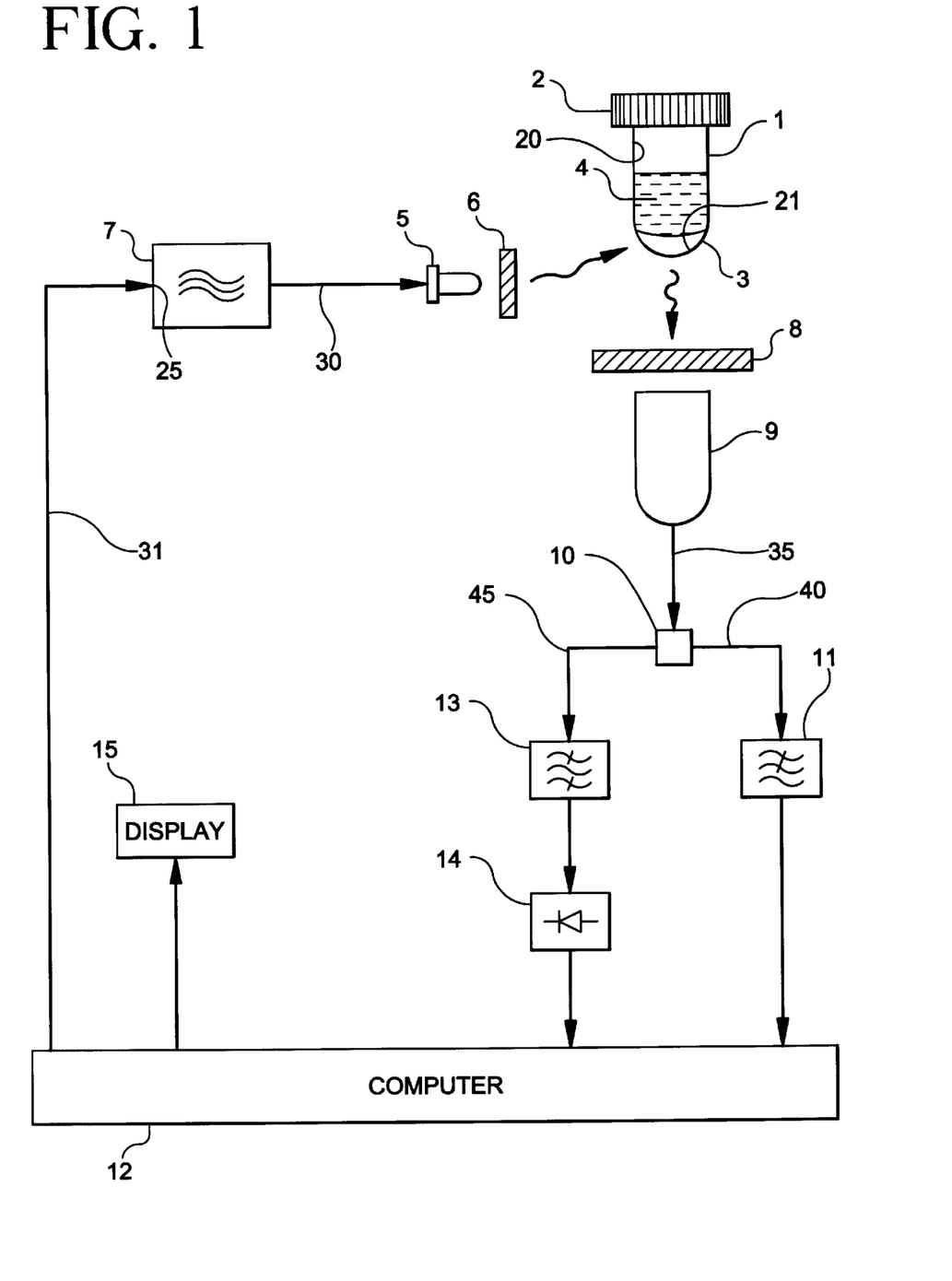
FIG. 1 shows schematically a composite optical blood culture sensor arrangement according to the present invention.

A preferred embodiment of a composite optical blood culture sensor arrangement embodying the principles and concepts of the invention is depicted schematically in FIG. 1. In this arrangement, a specimen and culture medium mixture 4 are introduced into an optically transparent container 1 that is sealed by a cap 2. A mixture of chemical sensor materials 3 is disposed to an inner wall 20 or an inner bottom surface 21 of container 1. The mixture 3 is illuminated by an excitation light source 5, preferably a blue LED 5, that is connected to an electronic signal source 7. Signal source 7 provides a DC bias and a high-frequency modulation voltage to light source 5 over a line 30, and is equipped with a power control input 25 connected by a line 31 to a computer 12.

Sensor material mixture 3 comprises a mixture of a fluorophore and a chromophore, wherein the fluorophore exhibits a long fluorescence decay time and a fluorescence intensity that depend on a first chemical parameter, such as oxygen concentration. The chromophore, however, exhibits an optical transmission that depends on a second chemical parameter, such as carbon dioxide concentration. The optical transmission of the chromophore changes with the second chemical parameter, either within the excitation or within the emission wavelength range of the fluorophore.

In a preferred embodiment, the fluorophore utilized in the present invention can be tris-4,7-diphenyl-1,10-phenanthroline ruthenium (II) chloride (produced by Becton Dickinson Microbiology Systems, Cockeysville, Md.). This fluorophore shows a fluorescence decay time and fluorescence intensity that decrease with increasing oxygen concentration. The fluorescence decay time in the absence of oxygen is approximately 5.5 $\mu s$, and decreases to approximately 0.7 $\mu s$ at 20% oxygen concentration. The fluorophore can absorb excitation light within the range 350 nm to 550 nm. The fluorescence emission spectrum reaches from 550 nm to 750 nm.

In a further preferred embodiment, the chromophore utilized can be Bromocresol Purple, m-Cresol Purple, Nitrazine Yellow, Chlorophenol Red, or Bromothymol Blue (which all can be obtained from Aldrich, Milwaukee, Wis.). These chromophores show optical transmission spectra that change in response to a changing pH value. The changes occur as well within the excitation region as within the emission region of the preferred fluorophore, tris-4,7-diphenyl-1,10-phenanthroline ruthenium (II) chloride, mentioned above. In the presence of water, a changing carbon dioxide concentration results in a pH change, and therefore in a change in the transmission of the chromophore. Consequently, these chromophores can be used to monitor either changes in pH or in carbon dioxide concentration, depending if water is present or not.

Further more, the fluorophores and chromophores which can be utilized in the present invention are not intended to be limited to the above embodiments. Today, numerous chemically sensitive chromophores and fluorophores are known and can be obtained from different suppliers. If, in the above-mentioned preferred fluorophore, tris-4,7-diphenyl-1,10-phenanthroline ruthenium (II) chloride, the metal ligand Ruthenium (Ru) is replaced with Palladium (Pd), a similar fluorophore is then obtained. This alternative fluorophore also has a long fluorescence decay time which allows one to use low-cost light-emitting diodes as excitation sources. The decay time and the fluorescence intensity are oxygen dependent. The difference is that the fluorophore comprising the Pd complex can be excited and emits at longer wavelengths, as compared to the fluorophore containing the Ru complex.

Fluorescence light reemerging from sensor material mixture 3 is detected by a photodetector 9, e.g., a photomultiplier. An emission filter 8 is arranged between mixture 3 and photodetector 9, and an excitation filter 6 is mounted in front of light source 5, to prevent excitation light from light source 5 reaching photodetector 9. Photodetector 9 generates an output signal on a line 35 that is fed to a power splitter 10. Power splitter 10 then generates two output signals, one of which is connected by a line 40 to the input of a low-pass filter 11 that is connected directly to computer 12. The other output signal of power splitter 10 is fed by a line 45 to the input of a band-pass filter 13 that is connected via a high-frequency voltmeter 14 to computer 12. Computer 12 is connected to a data display unit 15 to display information.

In operation, light source 5 illuminates sensor material mixture 3 with excitation light that is intensity-modulated at a circular modulation frequency, $\omega$, having a modulation degree, m. The emitted fluorescence intensity of sensor material mixture 3 can be described by:

$$F(t) = T(t) * F_0(t) \left[ 1 + \frac{m}{\sqrt{1 + (\omega\tau(t))^2}} \sin(\omega\tau - \theta(t)) \right] \quad (2)$$

with T(t) being the carbon dioxide-dependent optical transmission of the chromophore, $F_0(t)$ being the oxygen-dependent average fluorescence intensity, and $$\theta(t) = arc \tan [\omega\tau(t)] \quad (3)$$

being the fluorescence phase shift relative to the excitation modulation phase. In equation (2), m represents the modulation degree of the excitation light, which can be as high as 1. For all plots that follow, a constant source modulation degree, m=0.7, a very reasonable value, is assumed. The quantity $\tau(t)$ in equations (2) and (3) is fluorescence lifetime.

Figure 2:
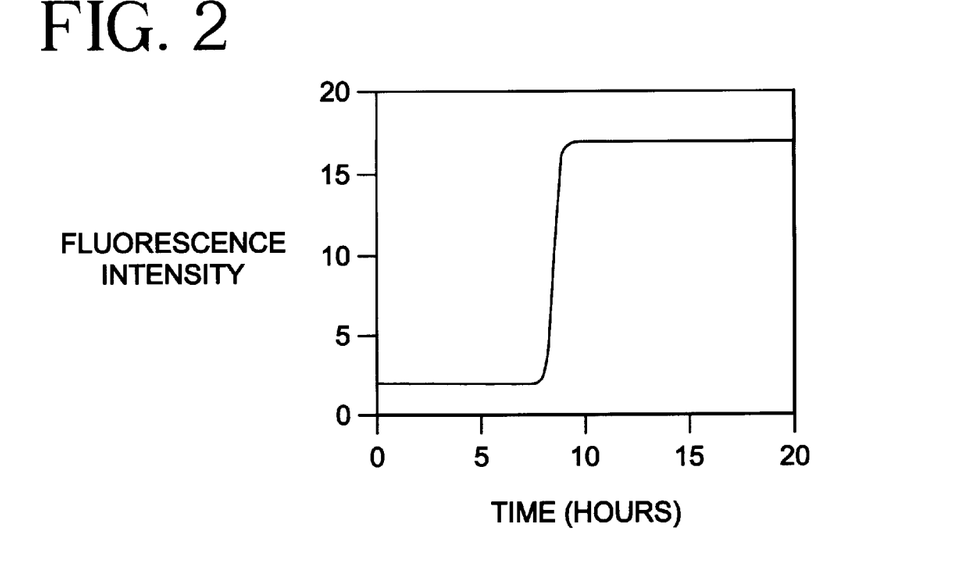
FIG. 2 is a plot showing fluorescence intensity versus time for the fluorophore, in response to oxygen consumption by the microorganisms.

Average fluorescence intensity, $F_0(t)$, may depend on time, t, according to the expression:

$$F_0(t) = k_1 \cdot h(t) \quad (4)$$

where $k_1$ is a constant, and h(t) is a time-dependent function that rises from a first, lower level to a second, higher level as a consequence of oxygen consumption during microorganism growth. FIG. 2 is a plot showing fluorescence intensity versus time for a fluorophore, in response to oxygen consumption by the microorganisms.

Fluorescence lifetime $\tau(t)$, may depend on time, t, according to the expression:

$$\tau(t) = k_2 \cdot h(t) \quad (5)$$

where $k_2$ is a constant, and h(t) is the same time-dependent function that rises from a first, lower level to a second, higher level as a consequence of oxygen consumption during microorganism growth.

Figure 3:
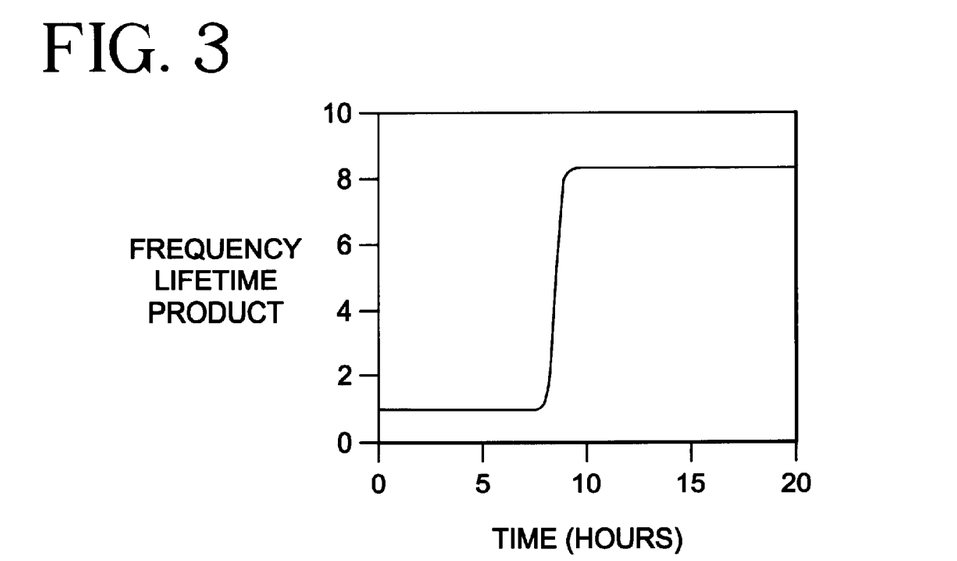
FIG. 3 is a plot showing frequency lifetime product, $\omega\tau$, versus time for the fluorophore, in response to oxygen consumption by the microorganisms.

Modulation frequency, $\omega$, is chosen so that the condition $\omega\tau \approx 1$ holds for the fluorophore when it has its minimum $\tau$-value. FIG. 3 is a plot showing frequency lifetime product, $\omega\tau$, versus time for the fluorophore, in response to oxygen consumption by the microorganisms. The light modulation frequency is selected so that $\omega\tau = 1$ prior to oxygen consumption if the fluorescence lifetime is short.

Figure 4:
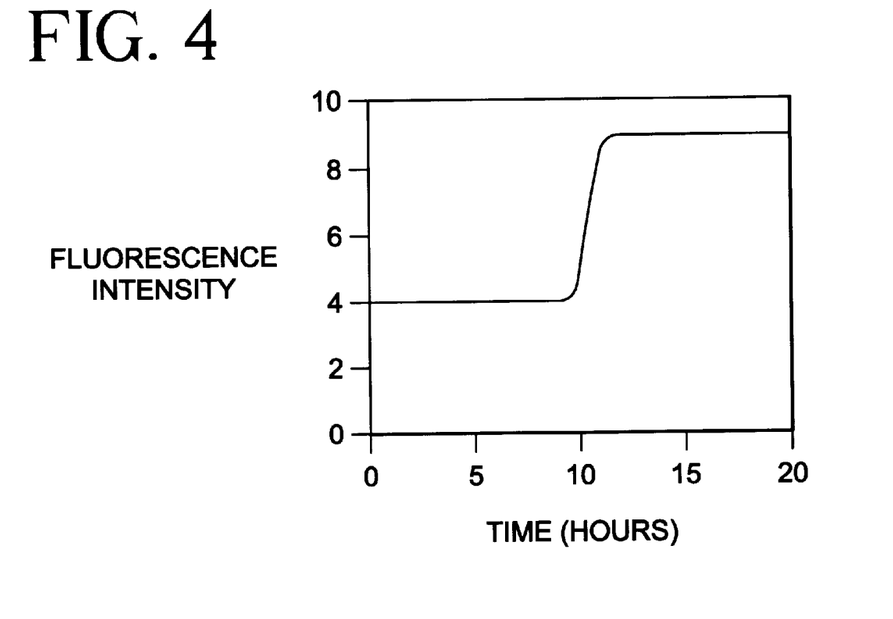
FIG. 4 is a plot showing fluorescence intensity versus time in response to carbon dioxide production.

Optical transmission of the chromophore, T(t), is also a time-dependent function that rises from a first, lower level to a second, higher level as a consequence of carbon dioxide production during microorganism growth. FIG. 4 is a plot showing the corresponding increase in the remitted fluorescence intensity versus time in response to carbon dioxide production. The carbon dioxide response exhibits a time delay relative to oxygen response.

In a composite optical blood culture sensor arrangement according to the present invention, the fluorescence photocurrent, I(t), is given by the expression:

$$I(t) = K \cdot F(t) \quad (6)$$

where K is a constant. Photocurrent I(t) is then split into AC and DC components that are measured separately, so that an AC/DC ratio can then be calculated within computer 12. Based on this, we obtain for the AC component:

$$AC = K * T(t) * F_0(t) \frac{m}{\sqrt{1 + (\omega\tau(t))^2}} \quad (7)$$

for the DC component:

$$DC = K \cdot T(t) \; F_0(t) \quad (8)$$

and for the fluorescence modulation degree:

$$\frac{AC}{DC} = \frac{m}{\sqrt{1 + (\omega\tau(t))^2}} \quad (9)$$

Figure 5:
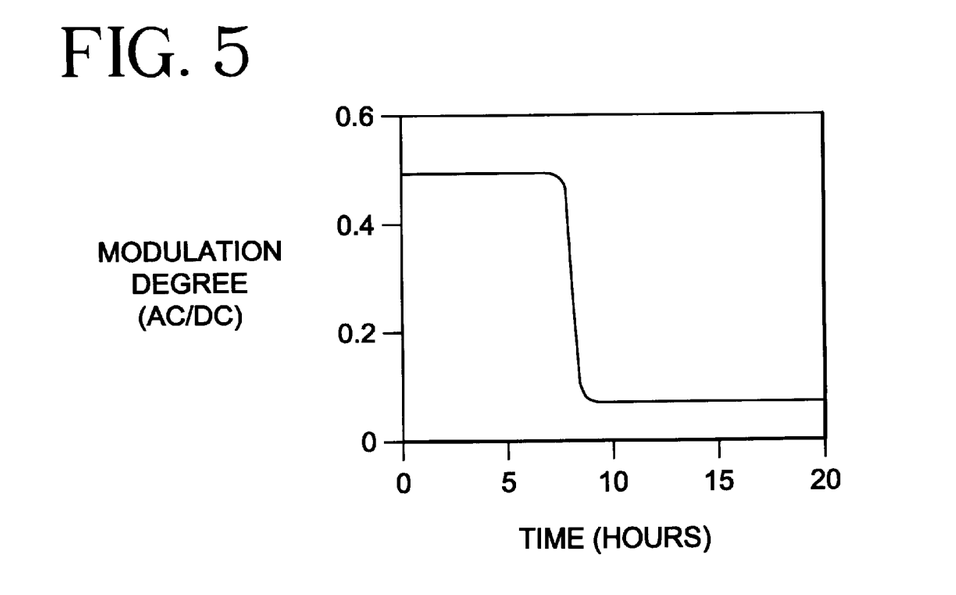
FIG. 5 is a plot showing modulation degree, AC/DC, of the fluorescence emission versus time in response to oxygen consumption and carbon dioxide production.

From equation (9), it can be seen that fluorescence modulation degree, AC/DC, does not change with a change in carbon dioxide concentration. This is illustrated in FIG. 5, where modulation degree, AC/DC, of the re-emitted fluorescence is plotted versus time, in response to oxygen consumption and carbon dioxide production. Equation (9) also shows that modulation degree, AC/DC, is independent of K, therefore, almost free from instrumental artifacts.

Figure 6:
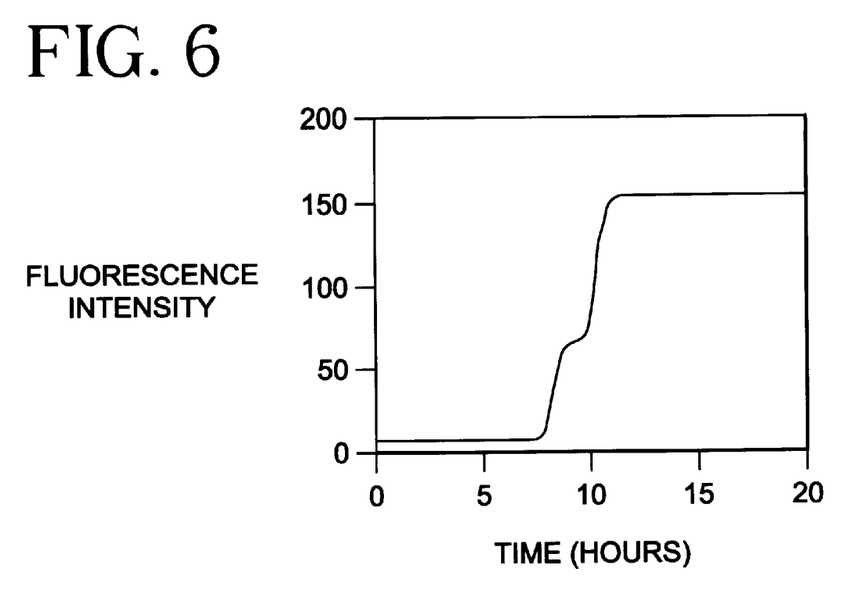
FIG. 6 is a plot showing fluorescence intensity versus time in response to oxygen consumption and delayed carbon dioxide production.

FIG. 6 is a plot of the DC signal, i.e., fluorescence intensity versus time in response to oxygen consumption and delayed carbon dioxide production. The contrast ratio due to the combined oxygen and carbon dioxide effect is 19.1, which is the product of the carbon dioxide contrast ratio of 2.25 and the oxygen contrast ratio of 8.5.

Figure 7:
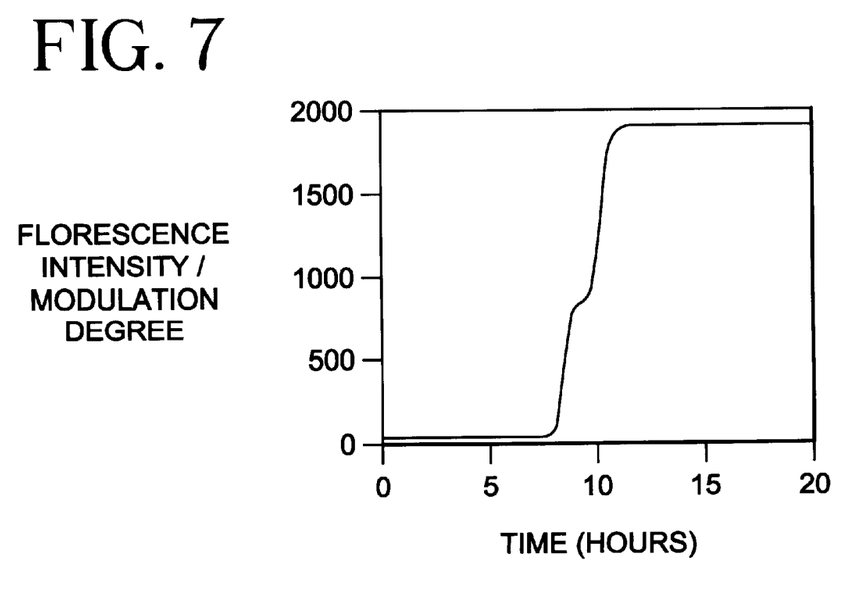
FIG. 7 is a plot showing fluorescence intensity divided by modulation degree versus time in response to oxygen consumption and delayed carbon dioxide production.

FIG. 7 is a plot showing fluorescence intensity, DC, divided by modulation degree, AC/DC, versus time in response to oxygen consumption and delayed carbon dioxide production. The plot in FIG. 7 represents a final sensor output signal that is displayed by computer 12 on display 15. It should be appreciated that the contrast ratio, relative to the contrast ratio in FIG. 6, is increased further from 19.1 to a value of 120.

Figure 8:
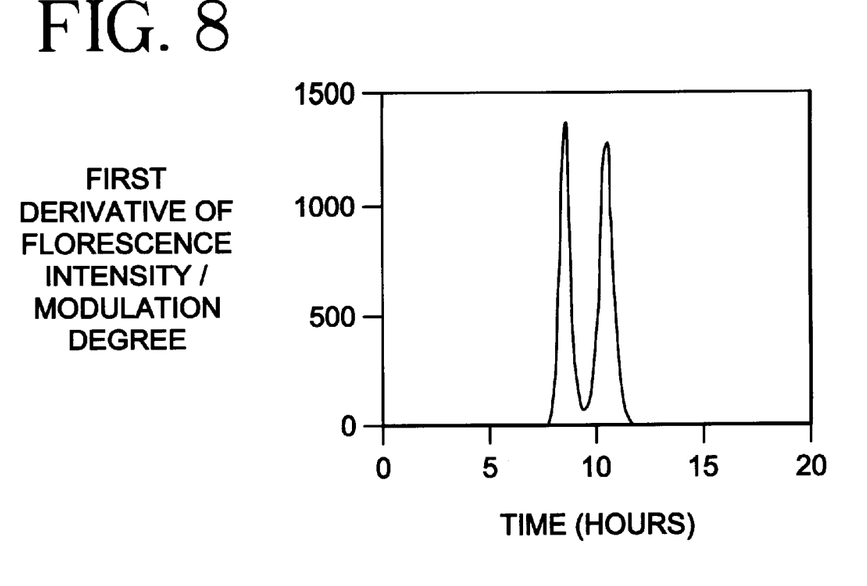
FIG. 8 is a plot showing the first derivative of the signal shown in FIG. 7.

FIG. 8 is a plot showing a first derivative of the signal in FIG. 7, and illustrates that the effects of oxygen consumption and carbon dioxide production are clearly separated. In this case, both peaks exhibit comparable heights.

Applicant has also found that the effects of oxygen consumption and carbon dioxide production can also be resolved, if no time delay should occur. This is possible simply by analyzing the final sensor output signal and the modulation degree, AC/DC. While final sensor output responds to both effects, modulation degree responds only to the oxygen effect. Therefore, it is possible to separate each effect.

Figure 9:
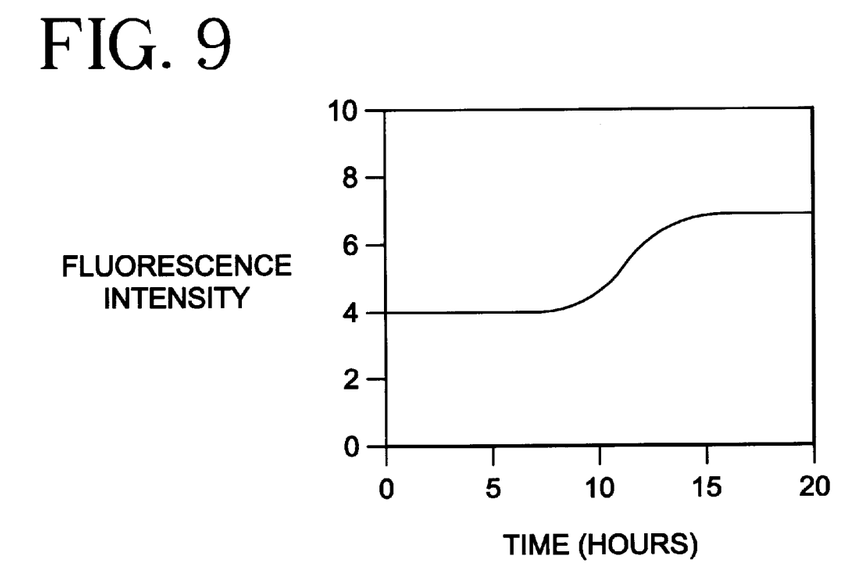
FIG. 9 is a plot showing fluorescence intensity versus time, like the plot shown in FIG. 4, but for a weak carbon dioxide producer.
Figure 10:
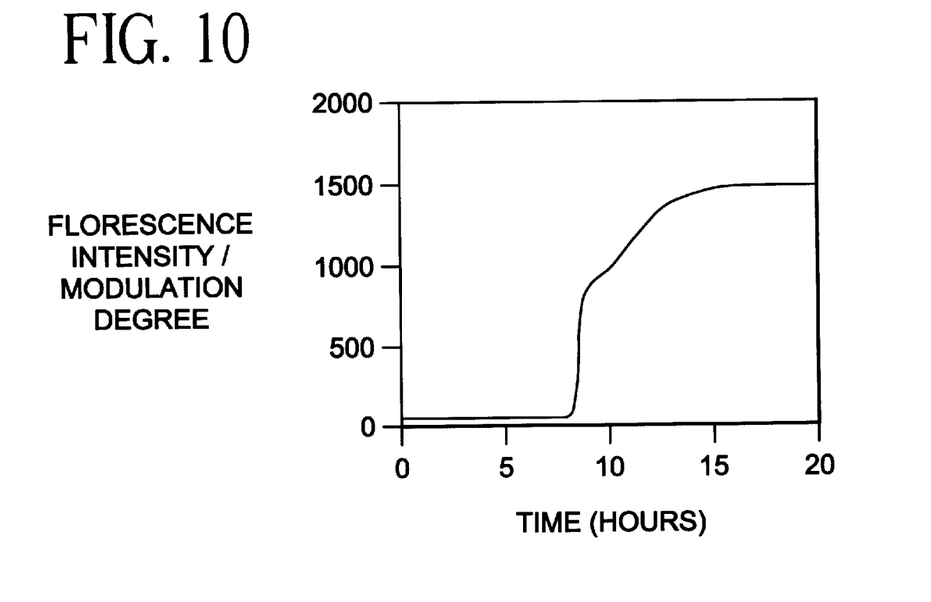
FIG. 10 is a plot showing fluorescence intensity divided by modulation degree versus time, like the plot shown in FIG. 7, but for a weak carbon dioxide producer.
Figure 11:
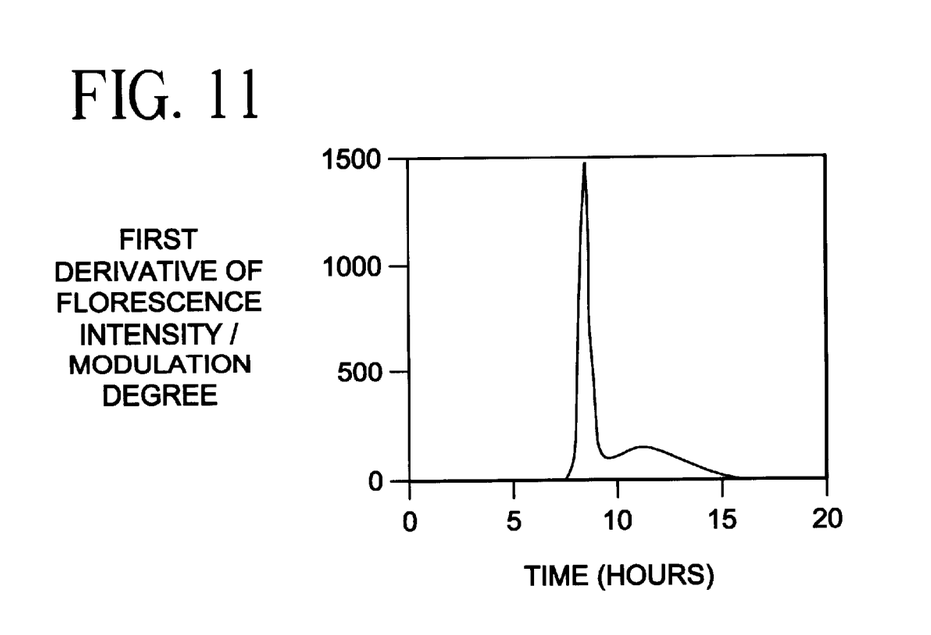
FIG. 11 is a plot showing the first derivative of the signal shown in FIG. 10, for the weak carbon dioxide producer.

FIG. 9 corresponds to FIG. 4, but shows a plot of fluorescence intensity versus time for a weak carbon dioxide producer; FIG. 10 corresponds to FIG. 7, but shows the final sensor output signal expected for a weak carbon dioxide producer; and FIG. 11 corresponds to FIG. 8, but shows the differentiated signal expected for a weak carbon dioxide producer. Again, the effects of oxygen consumption and carbon dioxide production are clearly separated, but now the two peaks exhibit very different heights.

Figure 12:
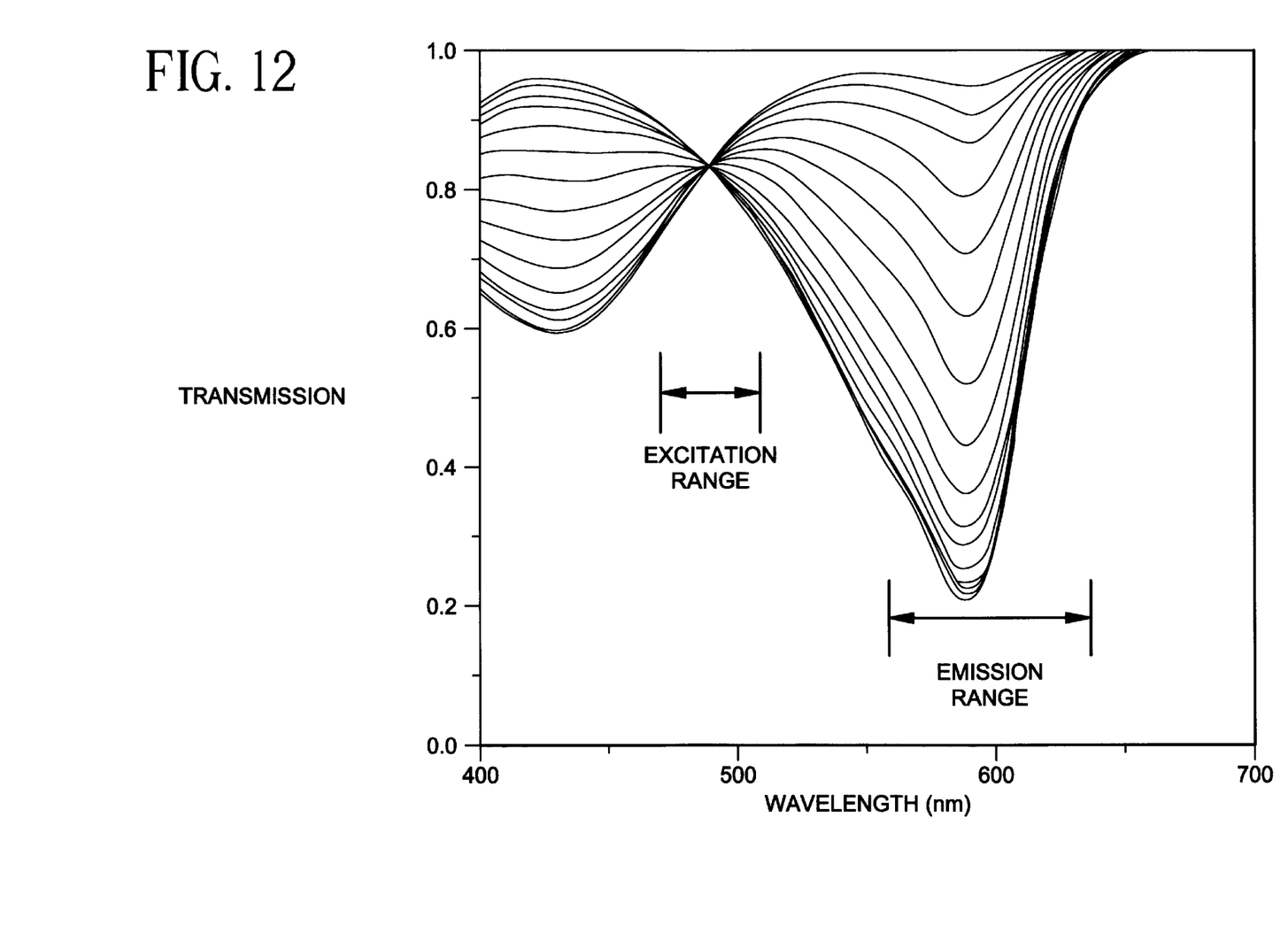
FIG. 12 is a plot showing standard spectral transmission characteristics for a pH/carbon dioxide-sensitive chromophore.

FIG. 12 is a plot showing a typical spectral transmission characteristic for a pH/carbon dioxide-sensitive chromophore. The family of curves shown in FIG. 12 illustrate the change in optical transmission with changing chemical input parameter, the indicated excitation range corresponding to the emission wavelength range of blue SiC light-emitting diodes. The indicated emission range corresponds to the emission wavelength range of available fluorescent oxygen sensors.

Figure 13:
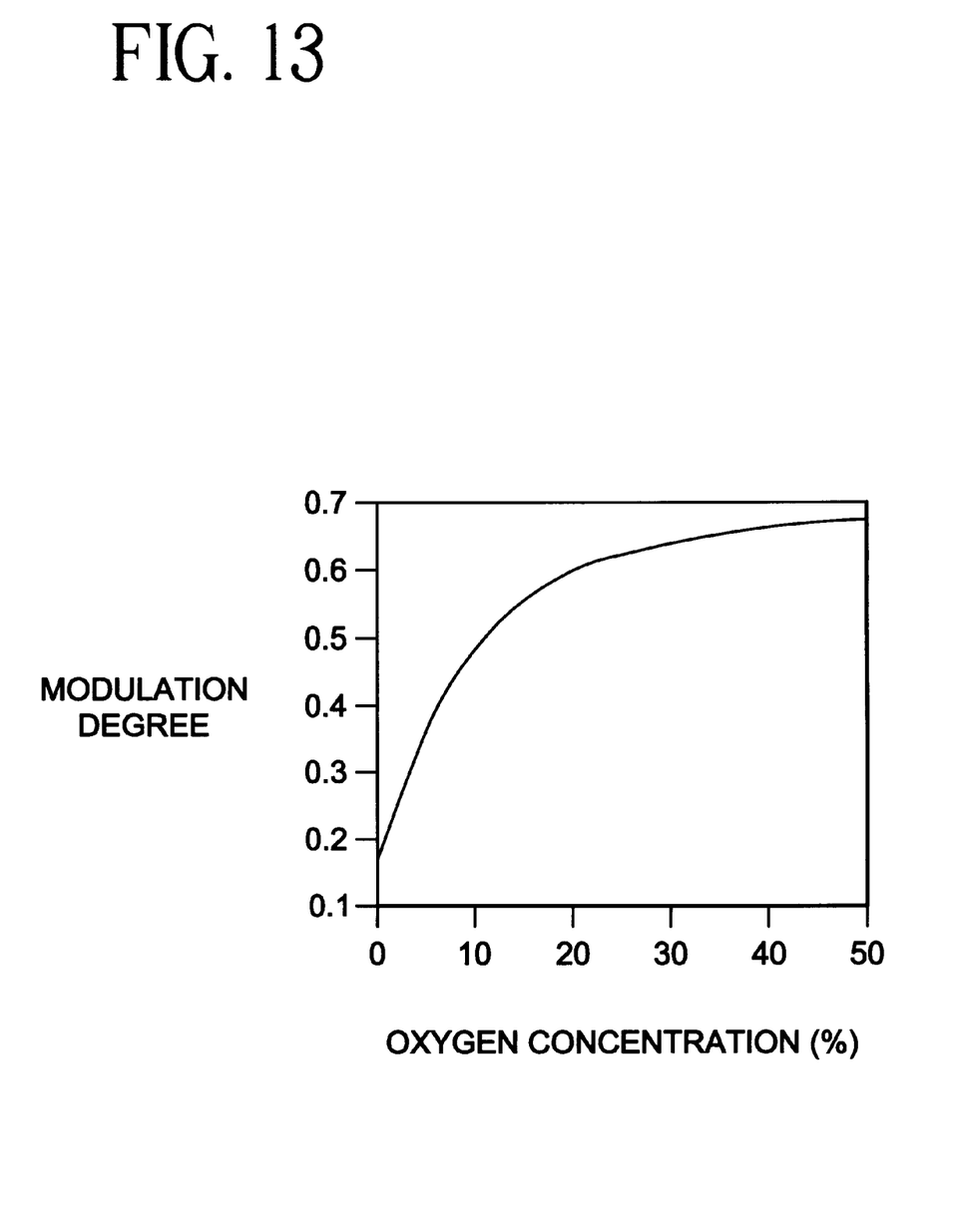
FIG. 13 is a plot showing modulation degree of the fluorescence emission for an oxygen sensor.

FIG. 13 shows the modulation degree, AC/DC, of a fluorescence emission for an oxygen sensor, the light modulation frequency having been set to 140 kHz. In this case, the condition $\omega\tau=1$ is fulfilled for an oxygen concentration of 11%. In doing so, changes in the initial high oxygen concentration have only a minor effect on the measured modulation degree. This is of advantage, in view of the required long shelf life of typical blood culture vials. In general, an optimization is possible by selecting a particular light modulation frequency.

Figure 14:
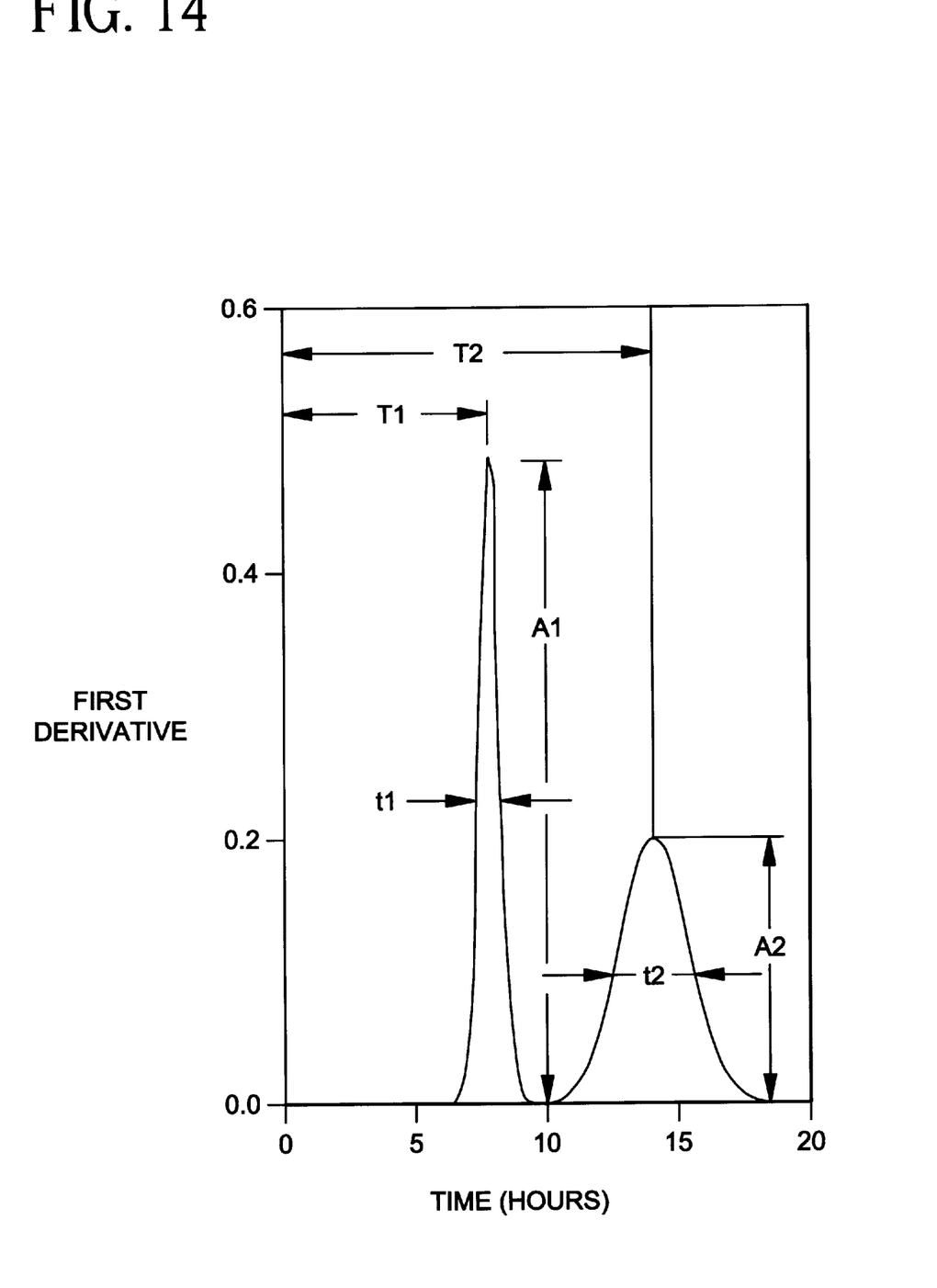
FIG. 14 is a plot showing the first derivative of a growth curve and its characteristic features.

FIG. 14 is a plot showing the first derivative of a growth curve and its characteristic features. In FIG. 14, T1 and T2 are the times of occurrence for the oxygen and the carbon dioxide effect. Parameters t1 and t2 indicate the duration for each of these effects and parameters A1 and A2 are related to the strength of both effects. Applicant has found that by compiling a set of these six characteristic parameters for each sample vial and comparing the set with the corresponding data base that has been generated using known samples at an earlier time, a presumptive microorganism identification can be achieved.

It should be understood that the above-described embodiment is simply illustrative of an apparatus embodying the principles and concepts of the present invention. For example, the mixture of chemical sensor materials 3, shown in FIG. 1, disposed to the wall or bottom surface of container 1 could be replaced with a bi-layer structure having the fluorophore and chromophore contained in two adjacent layers rather than mixed together. The chromophore would be attached first to container 1 and the fluorophore would then be added as a second top layer. While this may be a little more expensive because of the two production steps required, the effect of changing chromophore transmission on the emitted fluorescence would be even stronger, since every fluorescence excitation and/or emission photon would have to traverse the full chromophore layer. In the mixed option, shown in FIG. 1, some photons never "meet" a chromophore molecule, but only meet a fluorophore molecule to generate a new fluorescence photon and therefore leave the sensor material without interacting with any chromophore molecule. Of course, other suitable variations and modifications could also be made to the apparatus described and still remain within the scope of the present invention.

What is claimed is:

1. An apparatus for detecting microorganism growth comprising:

a container comprising a culture medium, a blood specimen, and a headspace having a concentration of a gas;

a chemically sensitive material in said container for detecting microorganism growth within said container when illuminated with an intensity-modulated light, said chemically sensitive material being comprised of a first material and a second material;

said first material exhibiting a fluorescence decay time and fluorescence intensity that depend on a first chemical parameter of said gas; and said second material exhibiting an optical transmission that depends on a second chemical parameter of said gas.

2. An apparatus according to claim 1, wherein said first chemical parameter of said gas is oxygen concentration, such that said first material exhibits a change in fluorescence decay time and fluorescence intensity in response to the change in oxygen concentration of said gas.

3. An apparatus according to claim 2, wherein said first material is a fluorophore.

4. An apparatus according to claim 3, wherein said fluorophore is tris-4,7-diphenyl-1,10-phenanthroline ruthenium (II) chloride.

5. An apparatus according to claim 1, wherein said second chemical parameter of said gas is carbon dioxide concentration, such that said second material exhibits a change in optical transmission in response to the change in carbon dioxide concentration of said gas.

6. An apparatus according to claim 5, wherein said second material is a chromophore.

7. An apparatus according to claim 6, wherein said chromophore is selected from the group consisting of bromocresol purple, m-cresol purple, nitrazine yellow, chlorophenol red or bromothymol blue.

8. An apparatus according to claim 5, wherein said second material exhibits a change in optical transmission within the excitation wavelength range or within the emission wavelength range of said first material, in response to the change in carbon dioxide concentration of said gas.

9. An apparatus according to claim 1, wherein:

said first material is a fluorophore that exhibits a change in fluorescence decay time and fluorescence intensity in response to a change in oxygen concentration of said gas; and said second material is a chromophore that exhibits a change in optical transmission in response to a change in carbon dioxide concentration of said gas, whereby the change in fluorescence intensity emitted by said fluorophore is amplified by the optical transmission change of said chromophore.

10. An apparatus according to claim 1, further comprising:

a light source for illuminating said chemically sensitive material in said container with excitation light that is intensity-modulated at a predetermined circular modulation frequency with a predetermined modulation degree;

a photodetector for detecting fluorescence light reemerging from said chemically sensitive material;

means for measuring an AC component and a DC component of the fluorescence photocurrent from said photodetector; and means for generating a sensor output signal based on the AC component and the DC component representing information as to whether or not microorganism growth is present within said container.

11. An apparatus according to claim 1, further comprising:

means for compiling a first set of signals corresponding to said fluorescence decay time and fluorescence intensity depending on said first chemical parameter of said gas;

means for compiling a second set of signals corresponding to said optical transmission depending on said second chemical parameter of said gas; and means for comparing the first and second sets of signals with a corresponding predetermined data base of first and second sets of signals for known microorganisms to perform microorganism identification on a detected microorganism.

12. An apparatus for detecting microorganism growth comprising:

a container comprising a culture medium, a blood specimen, and a headspace having a concentration of a gas;

a chemically sensitive material in said container for detecting microorganism growth within said container when illuminated with an intensity-modulated light, said chemically sensitive material being comprised of a first material and a second material;

said first material is a fluorophore that exhibits a change in fluorescence decay time and fluorescence intensity in response to a change in oxygen concentration of said gas;

said second material is a chromophore that exhibits a change in optical transmission in response to a change in carbon dioxide concentration of said gas, whereby the change in fluorescence intensity emitted by said fluorophore is amplified by the optical transmission change of said chromophore;

a light source for illuminating said chemically sensitive material in said container with the intensity-modulated light at a predetermined circular modulation frequency and a predetermined modulation degree;

a photodetector for detecting fluorescence light reemerging from said chemically sensitive material;

means for measuring an AC component and a DC component of the fluorescence photocurrent from said photodetector; and means for generating a sensor output signal based on the AC component and the DC component representing information as to whether or not microorganism growth is present within said container.

* * * * *